(12) United States Patent
Li et al.

(10) Patent No.: US 11,529,083 B2
(45) Date of Patent: Dec. 20, 2022

(54) PHYSIOLOGICAL STATUS EVALUATION METHOD AND PHYSIOLOGICAL STATUS EVALUATION APPARATUS

(71) Applicants: Acer Incorporated, New Taipei (TW); Taipei Veterans General Hospital, Taipei (TW); Acer Healthcare Inc., New Taipei (TW)

(72) Inventors: Chun-Hsien Li, New Taipei (TW); Tsung-Hsien Tsai, New Taipei (TW); Jun-Hong Chen, New Taipei (TW); Wei-Ting Wang, Taipei (TW); Yin-Hao Lee, Taipei (TW); Hao-Min Cheng, Taipei (TW)

(73) Assignees: Acer Incorporated, New Taipei (TW); Taipei Veterans General Hospital, Taipei (TW); Acer Medical Inc., New Taipei (TW)

( * ) Notice: Subject to any disclaimer, the term of this patent is extended or adjusted under 35 U.S.C. 154(b) by 177 days.

(21) Appl. No.: 17/083,340

(22) Filed: Oct. 29, 2020

(65) Prior Publication Data
US 2022/0079463 A1 Mar. 17, 2022

(30) Foreign Application Priority Data
Sep. 17, 2020 (TW) ................................ 109132117

(51) Int. Cl.
*A61B 5/316* (2021.01)
*A61B 5/00* (2006.01)
*A61B 5/318* (2021.01)

(52) U.S. Cl.
CPC .............. *A61B 5/316* (2021.01); *A61B 5/318* (2021.01); *A61B 5/7225* (2013.01); *A61B 5/7275* (2013.01)

(58) Field of Classification Search
CPC ....... A61B 5/316; A61B 5/318; A61B 5/7225; A61B 5/7275
See application file for complete search history.

(56) References Cited

U.S. PATENT DOCUMENTS

2007/0208232 A1* 9/2007 Kovacs ................. A61B 5/1118
600/595
2011/0066041 A1* 3/2011 Pandia ................... A61B 5/316
600/484
(Continued)

FOREIGN PATENT DOCUMENTS

| CN | 101785670 | 7/2010 |
| CN | 102973263 | 5/2014 |

(Continued)

*Primary Examiner* — Catherine M Voorhees
*Assistant Examiner* — Roland Dinga
(74) *Attorney, Agent, or Firm* — JCIPRNET

(57) ABSTRACT

A physiological status evaluation method and a physiological status evaluation apparatus are provided. The method includes the following: obtaining original electrocardiogram data of a user by an electrocardiogram detection apparatus; converting the original electrocardiogram data into digital integration data; obtaining a plurality of physiological characteristic parameters according to the digital integration data; filtering the physiological characteristic parameters for at least one notable characteristic parameter through at least one filter model, where decision importance of the at least one notable characteristic parameter in a decision process of the at least one filter model is greater than a threshold; building a prediction model according to the at least one notable characteristic parameter; and evaluating a physiological status of the user through the prediction model.

20 Claims, 6 Drawing Sheets

(56) References Cited

U.S. PATENT DOCUMENTS

| | | | | |
|---|---|---|---|---|
| 2013/0109946 A1* | 5/2013 | Shim | ................ | A61B 5/366 |
| | | | | 600/386 |
| 2017/0238858 A1* | 8/2017 | Yang | ................ | A61B 5/02416 |
| 2021/0315473 A1* | 10/2021 | Chan | ................ | A61B 5/7264 |

FOREIGN PATENT DOCUMENTS

| CN | 104398254 | 2/2017 |
|---|---|---|
| CN | 105105743 | 3/2017 |

\* cited by examiner

Tabular Summary

| Phase Name | Stage Name | Time in Stage | Speed (mph) | Grade (%) | Workload (METS) | HR (bpm) | BP (mmHg) | RPP (*100) | VE (l/min) | ST Level V4(mm) | Comment |
|---|---|---|---|---|---|---|---|---|---|---|---|
| PRETEST | SUPINE | 00:22 | 0.00 | 0.00 | 1.0 | 74 | | | 0 | 0.25 | |
| | | 00:24 | 0.00 | 0.00 | 1.0 | 78 | 136/73 | 103 | 0 | 0.30 | |
| EXERCISE | STAGE 1 | 03:00 | 1.70 | 10.00 | 4.6 | 96 | 132/76 | 126 | 0 | 0.45 | |
| | STAGE 2 | 03:00 | 2.50 | 12.00 | 7.0 | 106 | 137/79 | 145 | 0 | 0.25 | |
| | STAGE 3 | 03:00 | 3.40 | 14.00 | 10.1 | 120 | 140/84 | 175 | 0 | -0.75 | |
| | STAGE 4 | 01:44 | 4.20 | 16.00 | 12.9 | 139 | | | 5 | -2.40 | |
| RECOVERY | | 00:18 | 0.00 | 1.00 | 11.3 | 131 | 168/73 | 179 | 10 | -1.45 | |
| | | 01:00 | 0.00 | 0.00 | 6.3 | 107 | 174/76 | 153 | 3 | -0.40 | |
| | | 01:20 | 0.00 | 0.00 | 2.9 | 88 | 137/80 | 124 | 0 | -0.60 | |
| | | 04:49 | 0.00 | 0.00 | 1.0 | 91 | | | 3 | -0.15 | |
| | | 00:12 | 0.00 | 0.00 | 1.0 | 91 | | | 3 | -0.05 | |

Patient ID: 37
09/15/2011
1:59:15 pm

Male
54yrs Oriental
Meds:

Test Reason:
Medical History:

Ref. MD: 12073  Ordering MD:
Technician: CV 3651  Test Type:
Comment:

STA-2 Bruce  Total Exercise Time: 10:43
Max HR: 151 bpm  82% of max predicted 183 bpm
Max BP: 174/75  Maximum Workload: 12.90 METS
Max ST Level: -2.40 mm in V4 EXERCISE STAGE 4 10:44
Max TWA: 39 μV (II) ; EXERCISE 3:44
Reasons for Termination: Chest tightness
Location Number: * 2 *

PHYSIOLOGICAL STATUS EVALUATION METHOD AND PHYSIOLOGICAL STATUS EVALUATION APPARATUS

CROSS-REFERENCE TO RELATED APPLICATION

This application claims the priority benefit of Taiwan application serial no. 109132117, filed on Sep. 17, 2020. The entirety of the above-mentioned patent application is hereby incorporated by reference herein and made a part of this specification.

BACKGROUND

Technical Field

The disclosure relates to a physiological status evaluation technique, and in particular, to a physiological status evaluation method and a physiological status evaluation apparatus.

Description of Related Art

In conventional electrocardiogram detection, electrocardiogram data outputted by an electrocardiogram detection apparatus is required to be interpreted by a doctor. After blood pressure of a patent is measured, the doctor may confirm whether the patient has cardiovascular problems according to the electrocardiogram data and the blood pressure measurement results. Nevertheless, the electrocardiogram data and the blood pressure measurement results of different patients may lead to thousands of different combinations. Further, different doctors may produce different diagnosis results based on the same electrocardiogram data and blood pressure measurement results. Therefore, in practice, errors may occur in patients' cardiovascular diagnosis.

SUMMARY

The disclosure provides a physiological status evaluation method and a physiological status evaluation apparatus through which efficiency of physiological status evaluation of a user is improved.

An embodiment of the disclosure provides a physiological status evaluation method, and the method includes the following steps. Original electrocardiogram data of a user is obtained by an electrocardiogram detection apparatus. The original electrocardiogram data is converted into digital integration data. A plurality of physiological characteristic parameters are obtained according to the digital integration data. The physiological characteristic parameters are filtered for at least one notable characteristic parameter through at least one filter model, where decision importance of the at least one notable characteristic parameter in a decision process of the at least one filter model is greater than a threshold; A prediction model is built according to the at least one notable characteristic parameter. A physiological status of the user is evaluated through the prediction model.

An embodiment of the disclosure further provides a physiological status evaluation apparatus including a storage circuit and a processor. The storage circuit is configured to store original electrocardiogram data of a user obtained by an electrocardiogram detection apparatus. The processor is coupled to the storage circuit. The processor is configured to convert the original electrocardiogram data into digital integration data. The processor is further configured to obtain a plurality of physiological characteristic parameters according to the digital integration data. The processor is further configured to filter the physiological characteristic parameters for at least one notable characteristic parameter through at least one filter model. Herein, decision importance of the at least one notable characteristic parameter in a decision process of the at least one filter model is greater than a threshold. The processor is further configured to build a prediction model according to the at least one notable characteristic parameter. The processor is further configured to evaluate a physiological status of the user through the prediction model.

To sum up, after the original electrocardiogram data of the user is obtained through the electrocardiogram detection apparatus, the original electrocardiogram data may be converted into the digital integration data. According to the digital integration data, plural physiological characteristic parameters may be obtained. Next, the physiological characteristic parameters are filtered for the at least one notable characteristic parameter through the at least one filter model. In particular, the decision importance of the notable characteristic parameter in a decision process of the filter model is greater than the threshold. Next, one or plural prediction models may be built according to the notable characteristic parameter. In this way, the prediction model may be configured to evaluate the physiological status of the user hereinafter.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

FIG. 3 and FIG. 4 are schematic pictures illustrating original electrocardiogram data according to an embodiment of the disclosure.

FIG. 5 and FIG. 6 are schematic pictures illustrating text data according to an embodiment of the disclosure.

DESCRIPTION OF THE EMBODIMENTS

Figure 1:
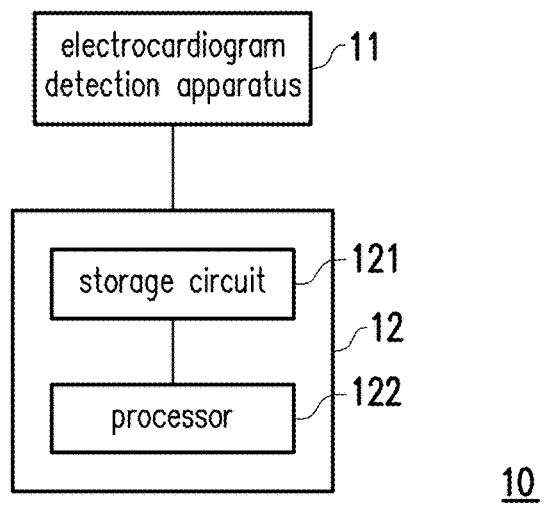
FIG. 1 is a schematic view illustrating a physiological status evaluation system according to an embodiment of the disclosure.

FIG. 1 is a schematic view illustrating a physiological status evaluation system according to an embodiment of the disclosure. With reference to FIG. 1, a physiological status evaluation system 10 includes an electrocardiogram detection apparatus 11 and a physiological status evaluation apparatus 12.

The electrocardiogram detection apparatus 11 may be configured to detect a cardiovascular status of a user in an exercise state and a non-exercise state and generate electrocardiogram data (also called as original electrocardiogram data) corresponding to the user. For instance, the original electrocardiogram data may include exercise electrocardiogram measurement data. The exercise electrocardiogram measurement data may reflect the cardiovascular status of the user during exercise, such as blood pressure and/or heart rate and the like. In addition, the original electrocardiogram data generated by the electrocardiogram detection apparatus 11 is outputted in a portable document format (PDF) or an image file format.

Figure 2:
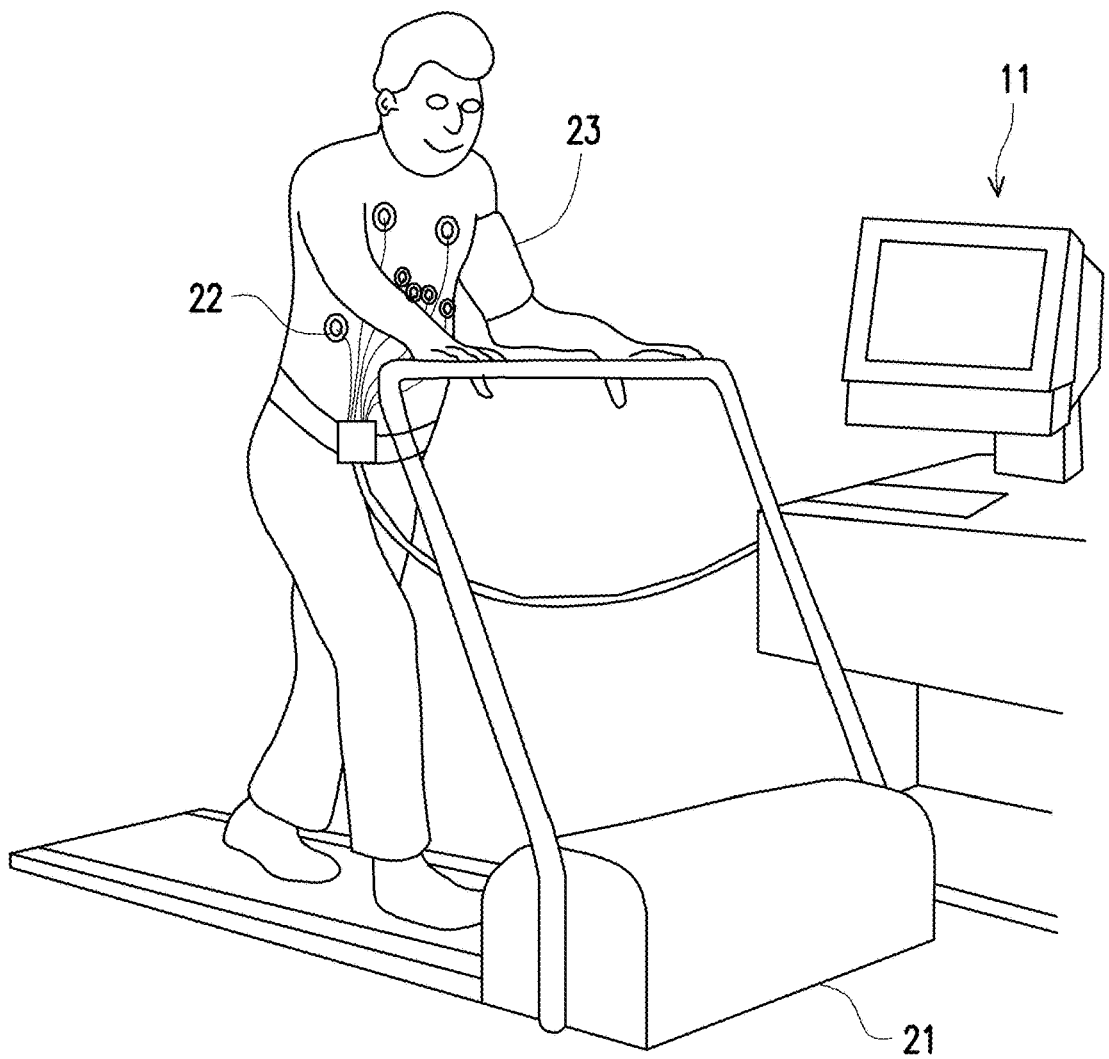
FIG. 2 is a schematic view illustrating detection of a cardiovascular status of a user by an electrocardiogram detection apparatus according to an embodiment of the disclosure.

FIG. 2 is a schematic view illustrating detection of a cardiovascular status of a user by an electrocardiogram detection apparatus according to an embodiment of the disclosure. With reference to FIG. 2, in an embodiment, a user may use exercise equipment such as a treadmill 21 to exercise. For instance, the user may walk or run on the treadmill 21 to be in the exercise state. When the user is in the exercise state, the electrocardiogram detection apparatus 11 may detect cardiovascular statuses of the user such as heart rate and blood pressure during exercise respectively through a heart rate sensor 22 and a blood pressure sensor 23. According to a detection result, the electrocardiogram detection apparatus 11 may output the original electrocardiogram data corresponding to this user. For instance, the electrocardiogram detection apparatus 11 may convert signals measured by the heart rate sensor 22 and the blood pressure sensor 23 into text or an image in the original electrocardiogram data and output the text or image.

With reference to FIG. 1 again, the physiological status evaluation apparatus 12 is coupled to the electrocardiogram detection apparatus 11. The physiological status evaluation apparatus 12 may evaluate a physiological status of the user according to the original electrocardiogram data generated by the electrocardiogram detection apparatus 11. For instance, this physiological status may reflect the user's cardiovascular health status and/or a risk or probability of suffering from a specific cardiovascular disease. In an embodiment, with further reference to personal data (e.g., age, height, weight, and/or gender and the like) and/or detection data (e.g., blood test data and/or urine test data and the like) of other types of the user, this physiological status may also reflect the physiological statuses of other aspects of the user, such as the overall health of the user and/or the risk or probability of the user suffering from a disease of a specific organ (e.g., liver, kidney, etc.).

The physiological status evaluation apparatus 12 includes a storage circuit 121 and a processor 122. The storage circuit 121 may include a volatile storage circuit and a non-volatile storage circuit. The volatile storage circuit is configured to temporarily store data in a volatile manner. For instance, the volatile storage circuit may include a random access memory (RAM). The non-volatile storage circuit is configured to temporarily store data in a non-volatile manner. For instance, the non-volatile storage circuit may include a solid state drive (SSD) and/or a conventional hard disk drive (HDD). The original electrocardiogram data generated by the electrocardiogram detection apparatus 11 may be stored in the storage circuit 121.

The processor 122 is coupled to the storage circuit 121. The processor 122 may be responsible for overall or partial operation of the physiological status evaluation apparatus 12. For instance, the processor 122 may include a central processing unit (CPU) or a programmable microprocessor for general or special use, a digital signal processor (DSP), a programmable controller, an application specific integrated circuit (ASIC), a programmable logic device (PLD), other similar devices, or a combination of the foregoing devices. The processor 122 may access the original electrocardiogram data in the storage circuit 121 and evaluate the physiological status of the user according to the original electrocardiogram data.

In an embodiment, the physiological status evaluation apparatus 12 may further include various input/output interface devices such as a mouse, a keyboard, a screen, a network interface card, and/or a power supply circuit and the like, which is not particularly limited by the disclosure. Besides, the physiological status evaluation apparatus 12 may be implemented as a computer apparatus of various types such as a desktop computer, a tablet computer, a notebook computer, an industrial computer, or a server, which is not particularly limited by the disclosure.

After obtaining the original electrocardiogram data, the processor 122 may convert the original electrocardiogram data into digital integration data. For instance, the processor 122 may retrieve required information from the original electrocardiogram data and integrate the information to generate the digital integration data. The digital integration data may record descriptive data related to a physiological characteristic of the user, such as blood pressure, heart rate, age, and/or weight and the like of the user, in a computer-readable format.

In an embodiment, the processor 122 may convert the original electrocardiogram data into text data. For instance, it is assumed that the file format of the original electrocardiogram data is PDF or a file format of a specific image file, so that the file format of the digital integration data may be a comma-separated value (CSV) or a text file (TXT), etc. The processor 122 may retrieve the descriptive data related to the physiological characteristic of the user from the text data according to a predetermined rule. The processor 122 may generate the digital integration data according to the retrieved descriptive data.

Figure 4:
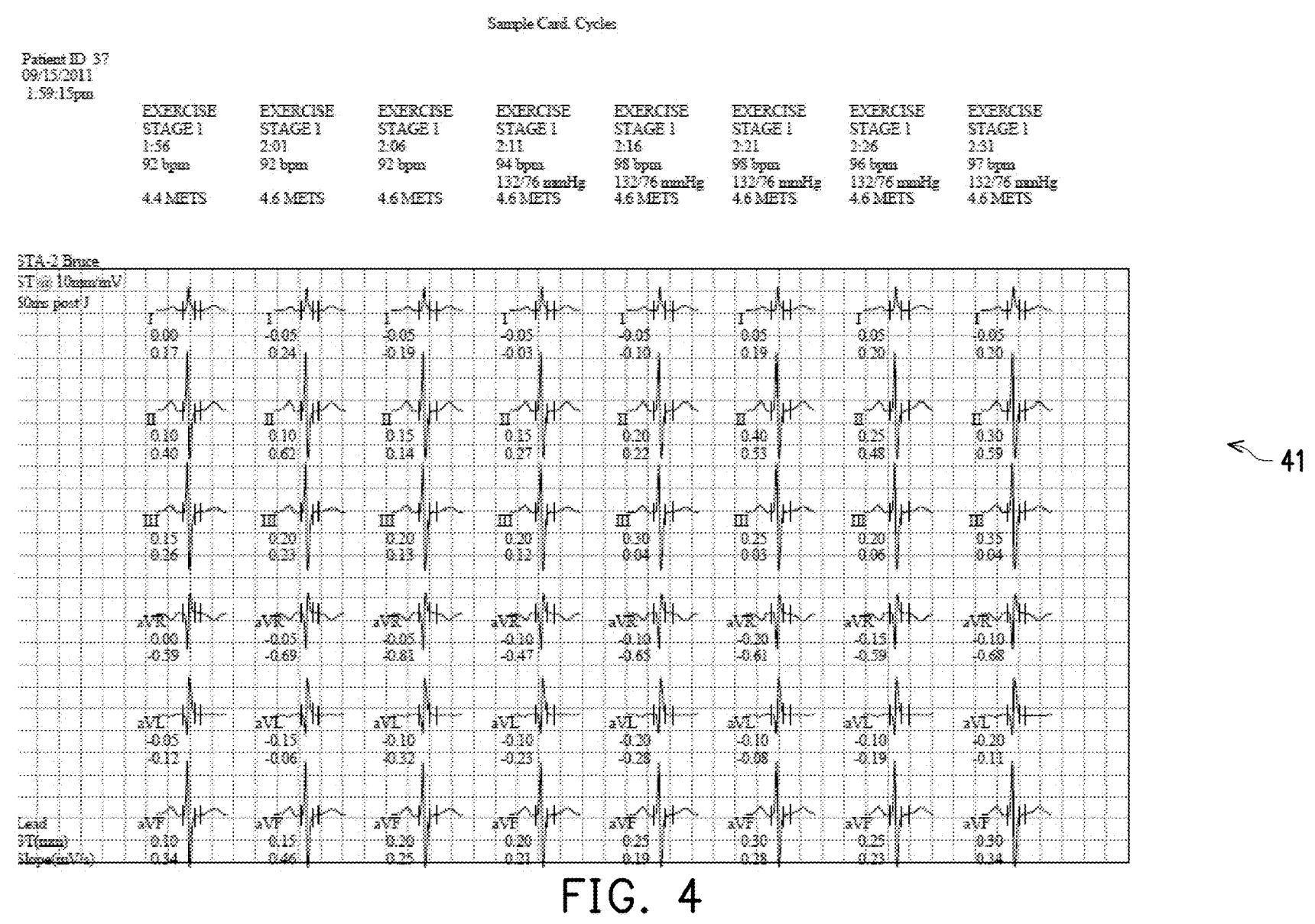
Figures 5, 6:
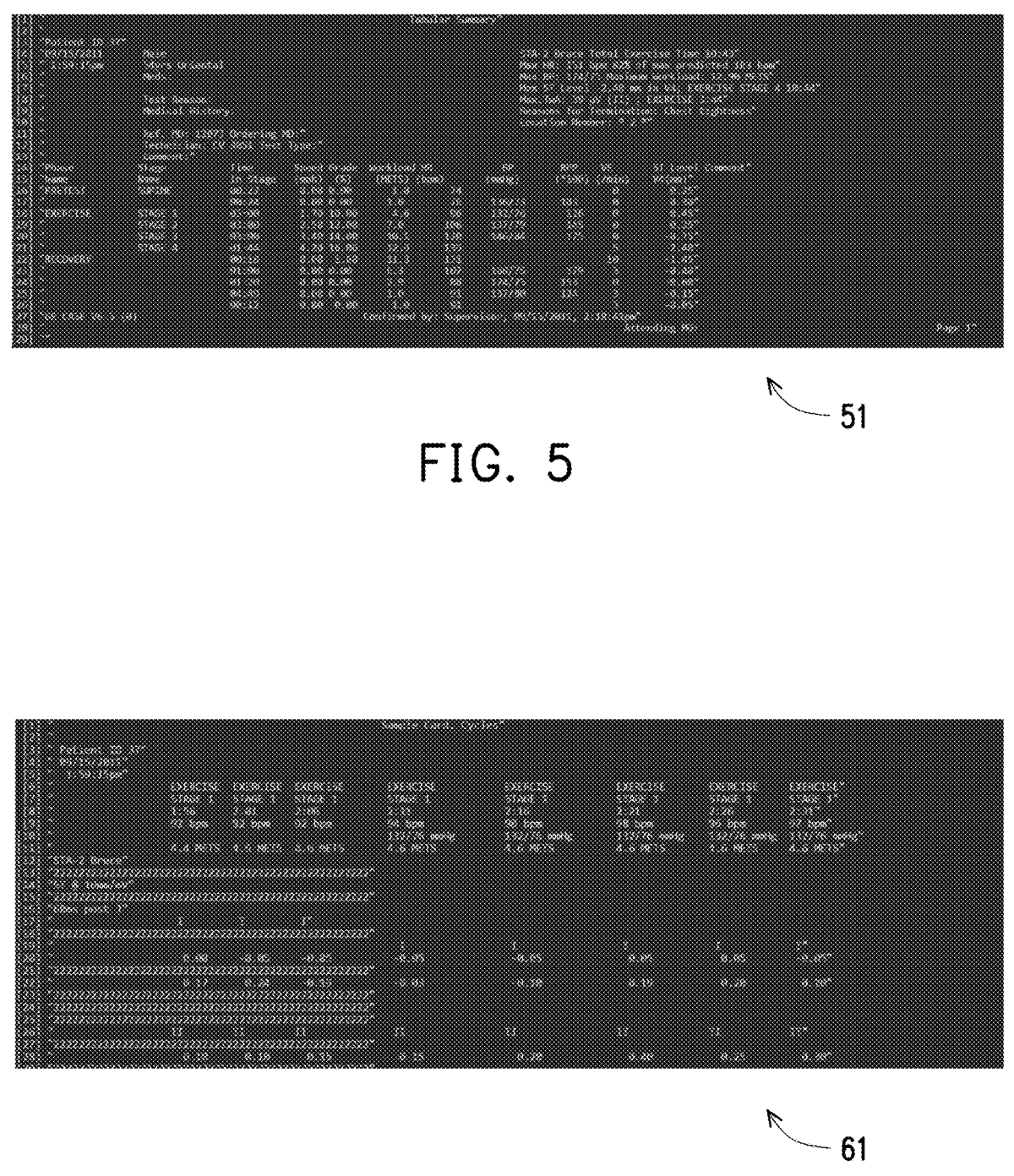

FIG. 3 and FIG. 4 are schematic pictures illustrating original electrocardiogram data according to an embodiment of the disclosure. FIG. 5 and FIG. 6 are schematic pictures illustrating text data according to an embodiment of the disclosure. With reference to FIG. 3 to FIG. 6, the original electrocardiogram data may include PDF files 31 and 41. The PDF files 31 and 41 present information such as age, gender, blood pressure, heart rate, and measurement time of a user. The processor 122 may retrieve the required information from the PDF files 31 and 41 according to an image-text conversion technique such as image recognition and the like and generate the text data according to the retrieved information. For instance, the generated text data includes text files 51 and 61 in FIG. 5 and FIG. 6. The text files 51 and 61 respectively reflect related text content in the PDF files 31 and 41 in a text form.

In an embodiment, the processor 122 may detect at least one keyword in the text data and retrieve descriptive data (also called as first descriptive data) corresponding to the keyword. Taking FIG. 5 as an example herein, the processor 122 may detect keywords "yrs", "Max BP", and "Max ST Level" in the text file 51 and obtain the first description data corresponding to the keywords. The retrieved first description data may be recorded as shown in Table 1 below. Other useful descriptive data may also be retrieved from the text data through the keyword detection manner provided above.

TABLE 1

| Keyword | yrs | Max BP | Max ST Level |
|---|---|---|---|
| Descriptive Data | 54 | 174/75 | −2.40 |

In an embodiment, the processor 122 may retrieve the descriptive data (also called as second descriptive data) in the retrieved text data according to the predetermined field format. Taking FIG. 5 as an example, the processor 122 may retrieve the corresponding second descriptive data from the text file 51 according to predetermined character lengths of different data fields such as "Phase Name", "Stage Name", and "Time in Stage". The retrieved second descriptive data may be recorded and as shown in Table 2 below. Other useful descriptive data may also be retrieved from the text data through the predetermined field format detection manner provided above.

TABLE 2

| Phase Name | Stage Name | Time in Stage |
|---|---|---|
| PRETEST | SUPINE | 00:22 |
| blank | blank | 00:24 |
| EXERCISE | STAGE 1 | 03:00 |
| blank | STAGE 2 | 03:00 |
| blank | STAGE 3 | 03:00 |
| blank | STAGE 4 | 01:44 |

In an embodiment, the processor 122 may detect a blank data region in the text data and retrieve descriptive data (also called as third descriptive data) recorded in this blank data region. Taking FIG. 6 as an example, the processor 122 may retrieve the third descriptive data behind the blank data region according to the blank data region which does not regularly appear in the text file 51. The retrieved third descriptive data may be recorded and as shown in Table 3 below. Other useful descriptive data may also be retrieved from the text data through the blank data region detection manner provided above.

TABLE 3

| EXERCISE STAGE 1 | EXERCISE STAGE 1 | EXERCISE STAGE 1 | EXERCISE STAGE 1 |
|---|---|---|---|
| 1:56 | 2:01 | 2:06 | 2:11 |
| 92 | 92 | 92 | 94 |
| blank | blank | blank | 132/76 |
| 4.4 | 4.6 | 4.6 | 4.6 |

In an embodiment, the processor 122 may generate the digital integration data as shown in Table 4 and/or Table 5 according to the retrieved descriptive data. For instance, the digital integration data in Table 4 records physiological characteristic parameters such as "Age", "Max BP", and "Max ST Level" of plural users. The digital integration data in Table 5 records the physiological characteristic parameters such as blood pressure, heart rate, and ST segment difference measured by the user with the number "1" at different measurement times and different test stages. Herein, "before testing" and "recovery period" indicate that the user is in the non-exercise state, and "during testing" indicate that the user is in the exercise state. In addition, other useful information may also be recorded in the digital integration data.

TABLE 4

| User ID | Age | Max BP | Max ST Level |
|---|---|---|---|
| 100001 | 54 | 174/75 | −2.40 |
| . . . | . . . | . . . | . . . |
| 100100 | 68 | 155/66 | −0.22 |

TABLE 5

| User | Systolic Pressure | Diastolic Pressure | Heart Rate | ST Segment Difference | Measurement Time | Detection Phase |
|---|---|---|---|---|---|---|
| 1 | 138 | 79 | 70 | 0.02 | 11:10 | before testing |
| 1 | 144 | 79 | 71 | 0.15 | 11:12 | before testing |
| 1 | 147 | 99 | 74 | 0.23 | 11:14 | during testing |
| 1 | 148 | 100 | 76 | 0.10 | 11:16 | during testing |
| 1 | 150 | 75 | 89 | 0.08 | 11:18 | during testing |
| 1 | 155 | 81 | 91 | 0.06 | 11:20 | during testing |
| 1 | 156 | 76 | 100 | −0.07 | 11:22 | during testing |
| 1 | 160 | 76 | 155 | −0.03 | 11:23 | during testing |
| 1 | 127 | 85 | 79 | −0.04 | 11:24 | recovery period |
| 1 | 140 | 80 | 76 | 0.06 | 11:25 | recovery period |
| 1 | 139 | 76 | 75 | 0.17 | 11:30 | recovery period |

In an embodiment, the processor 122 may obtain a number of occurrences of predetermined data in the retrieved descriptive data. Next, the processor 122 may verify whether the digital integration data is valid data according to this number of occurrences. For instance, the processor 122 may calculate the numbers of occurrences of at least one keyword in the original electrocardiogram data (or text data) and the retrieved descriptive data. If a difference between the numbers of occurrences of these keywords in the original electrocardiogram data and the retrieved descriptive data is not significant (e.g., not greater than a difference threshold), the processor 122 may then determine that the digital integration data is valid data. In contrast, if the difference between the numbers of occurrences of these keywords in the original electrocardiogram data and the retrieved descriptive data is significant (e.g., greater than the difference threshold), the processor 122 may then determine that the digital integration data is not valid data. If it is determined that the digital integration data is not valid data, the processor 122 may then re-execute the operation of converting the original electrocardiogram data into the digital integration data and/or executes other error processing operations, and description thereof is not repeated herein.

Taking FIG. 3 and FIG. 4 for example, the predetermined data may refer to a specific keyword, such as "Tabular Summary", "Sample Card. Cycles", "Phase Name", and "EXERCISE". The numbers of occurrences of these keywords in the original electrocardiogram data (or text data) and the retrieved descriptive data may be recorded as shown in Table 6 below.

TABLE 6

| Keyword | Number of Occurrences in Original Electrocardiogram Data | Number of Occurrences in Digital Integration Data |
|---|---|---|
| Tabular Summary | 1 | 1 |
| Sample Card. Cycles | 1 | 1 |
| Phase Name | 5 | 4 |
| EXERCISE | 20 | 19 |

The processor 122 may calculate a parameter D configured to calculate a difference degree according to Table 6, and D=((1−1)+(1−1)+(5−4)+(20−19))/4=0.5, for example. If the parameter D is not greater than a difference threshold X (e.g., 2), the processor 122 may determine that the generated digital integration data is valid data. In contrast, if the parameter D is greater than the difference threshold X (e.g., 2), the processor 122 may determine that the generated digital integration data is not valid data.

In an embodiment, the processor 122 may obtain plural physiological characteristic parameters according to the digital integration data (e.g., the digital integration data determined to be valid data). For instance, the physiological characteristic parameters include a time-related characteristic parameter and a logic-related characteristic parameter. The time-related characteristic parameter reflects a physiological characteristic of the user measured at a plurality of time points. The logic-related characteristic parameter reflects a physiological characteristic of the user matched with a logistic condition. Taking Table 5 as an example, the time-related characteristic parameter may include physiological characteristic parameters such as systolic pressure, diastolic pressure, heart rate, and ST segment difference tested at different time points and/or different testing phases. In addition, the logic-related characteristic parameter may include characteristic parameters generated by logical analysis of physiological characteristic parameters in a single testing phase or across testing phases.

In an embodiment, with reference to Table 5 together, the logic-related characteristic parameter may include a maximum systolic pressure before testing (e.g., 144), heart rate average value during testing (e.g., 97.5), maximum heart rate ratio (e.g., 155 (i.e., a maximum heart rate during testing)/170 (i.e., expected heart rate 220-age)=91.2%), a maximum systolic pressure (e.g., 160), a maximum ST segment difference (e.g., 0.23), a maximum descending slope of heart rate before testing and during testing (e.g., 1−(155/70)=−1.21), and/or a time difference between maximum heart rate differences before testing and during testing (e.g., 13 minutes). Note that the time-related characteristic parameter and the logic-related characteristic parameter are provided to serve as examples only, and the adopted time-related characteristic parameter and/or the logic-related characteristic parameter may further be adjusted in practice.

After obtaining the physiological characteristic parameters, the processor 122 may further filter the physiological characteristic parameters for at least one notable characteristic parameter through at least one filter model. The filter model may be stored in the storage circuit 121. For instance, the filter model may include at least one of a support vector machine (SVM) model, a one class SVM model, a random forest model, and a logistic classification model, and a type of the filter model is not particularly limited.

Note that decision importance of the notable characteristic parameter in a decision process of the at least one filter model is greater than a threshold. In other words, in the decision process of the at least one filter model, importance and/or influence of the notable characteristic parameter to the decision process is generally greater than importance and/or influence of the rest of the physiological characteristic parameters.

In an embodiment, the processor 122 may input the obtained physiological characteristic parameters into the at least one filter model for processing. Next, the processor 122 may, according to a degree of participation of a specific physiological characteristic parameter (also called as a first physiological characteristic parameter) among the physiological characteristic parameters in the decision process of the at least one filter model, determine an importance evaluation value corresponding to the first physiological characteristic parameter. The processor 122 may determine the first physiological characteristic parameter as one of the at least one notable characteristic parameter if the importance evaluation value is greater than an evaluation threshold.

In an embodiment, the processor 122 may record results of whether physiological characteristic parameters P1 to P5 are selected as physiological characteristic parameters with greater decision importance (e.g., greater than the threshold) in decision processes repeated twice of 3 filter models M1 to M3 in Table 7 provided below. For instance, according to Table 7, the physiological characteristic parameter P1 is selected as the physiological characteristic parameter with greater decision importance in all of the decision processes repeated twice of the filter models M1 to M3. The physiological characteristic parameter P2 is selected as the physiological characteristic parameter with greater decision importance in only a first decision process in each of the filter models M1 and M2, and the rest may be deduced by analogy.

TABLE 7

| Characteristic Parameter | First Decision of M1 | Second Decision of M1 | First Decision of M2 | Second Decision of M2 | First Decision of M3 | Second Decision of M3 |
|---|---|---|---|---|---|---|
| P1 | 1 | 1 | 1 | 1 | 1 | 1 |
| P2 | 1 | 0 | 1 | 0 | 0 | 0 |
| P3 | 0 | 0 | 1 | 1 | 0 | 0 |
| P4 | 0 | 0 | 0 | 0 | 0 | 1 |
| P5 | 1 | 0 | 0 | 0 | 0 | 1 |

In an embodiment, according to the information provided in Table 3, the processor 122 may record the numbers and probabilities of the physiological characteristic parameters P1 to P5 being selected by the filter models M1 to M3 and generated importance evaluation values in Table 8 below. Taking the physiological characteristic parameter P1 as an example, the importance evaluation value of the physiological characteristic parameter P1 may be obtained according to $((1 \times \frac{1}{3})+(1 \times \frac{1}{3})+(1 \times \frac{1}{3})=1)$, the importance evaluation value of the physiological characteristic parameter P2 may be obtained according to $((0.5 \times \frac{1}{3})+(0.5 \times \frac{1}{3})+(0 \times \frac{1}{3})=\frac{1}{3})$, and the rest may be deduced by analogy. It is assumed that the evaluation threshold is "$\frac{1}{3}$", so the processor 122 may determine the physiological characteristic parameters P1 to P3 and P5 with importance evaluation values greater than "$\frac{1}{3}$" as the notable characteristic parameters.

TABLE 8

| Physiological Characteristic Parameter | Number of Times Selected by M1 | Number of Times Selected by M2 | Number of Times Selected by M3 | Probability of Being Selected by M1 | Probability of Being Selected by M2 | Probability of Being Selected by M3 | Importance Evaluation Value |
|---|---|---|---|---|---|---|---|
| P1 | 2 | 2 | 2 | 1.0 | 1.0 | 1.0 | 1 |
| P2 | 1 | 1 | 0 | 0.5 | 0.5 | 0.0 | $\frac{1}{3}$ |
| P3 | 0 | 2 | 0 | 0.0 | 1.0 | 0.0 | $\frac{1}{3}$ |
| P4 | 0 | 0 | 1 | 0.0 | 0.0 | 0.5 | $\frac{1}{6}$ |
| P5 | 1 | 0 | 1 | 0.5 | 0.0 | 0.5 | $\frac{1}{3}$ |

After determining the notable characteristic parameter, the processor 122 may build at least one prediction model according to the notable characteristic parameter. In this way, the processor 122 may evaluate the physiological status of the user thorough the built prediction model hereinafter.

In an embodiment, the processor 122 may input the notable characteristic parameter into at least one candidate model for processing. The candidate model may be stored in the storage circuit 121. For instance, the candidate model may include at least one of a long short term memory (LSTM) model, an SVM model, a one class SVM model, a random forest model, and a logistic classification model, and a type of the candidate model is not particularly limited. According to a processing result, the processor 122 may compare prediction accuracy of the at least one candidate model with an accuracy threshold. If prediction accuracy (also called as first prediction accuracy) of a specific candidate model (also called as a first candidate model) among the at least one candidate model is greater than the accuracy threshold, the processor 122 may determine the first candidate model as the prediction model to be built.

In an embodiment, the prediction accuracy is presented by at least one of sensitivity, specificity, a positive predictive value (PPV), a negative predictive value (NPV), a positive likelihood ratio (LR+), and a negative likelihood ratio (LR−).

In other words, according to prediction results of prediction run by different candidate models by using the notable characteristic parameter, the processor 122 may obtain the prediction accuracy of prediction run by different candidate models by using the notable characteristic parameter. In an embodiment, it is assumed that LR+ acts as a type of representing the prediction accuracy, so the prediction accuracy of a specific candidate model (e.g., the random forest model) using the notable characteristic parameter may be represented by the numerical value of "1.65", and the prediction accuracy of another candidate model (e.g., the LSTM model) using the same notable characteristic parameter may be represented by the numerical value of "2.75". In this embodiment, the prediction accuracy of the LSTM model is greater than the prediction accuracy of the random forest model. Therefore, the processor 122 may build the final prediction model to be used according to the LSTM model.

In an embodiment, the processor 122 may configure the accuracy threshold according to a conventionally-used Treadmill scoring method. For instance, the Treadmill scoring method may directly analyze the original electrocardiogram data and generates a corresponding LR+ score. In practice, a doctor may evaluate the quality of a prediction model currently in use according to such a LR+ score. Alternatively, a doctor may also evaluate whether to perform surgery on a patient according to this LR+ score. It is assumed that the LR+ obtained through the conventional Treadmill scoring method is "2.70", so that the accuracy threshold may be configured to be "2.70". In an embodiment, the prediction accuracy (e.g., "1.65") of the random forest model is not greater than this accuracy threshold, but the prediction accuracy (e.g., "2.75") of the LSTM model is greater than this accuracy threshold. In this way, the processor 122 may build the final prediction model to be used according to the LSTM model. In addition, the accuracy threshold may also be configured according to other mechanisms, which is not particularly limited by the disclosure.

In an embodiment, the processor 122 may interactively compare the prediction accuracy of prediction run by multiple candidate models by using the notable characteristic parameter and/or compares the prediction accuracy of prediction run by multiple candidate models by using the notable characteristic parameter with a single accuracy threshold, which is not particularly limited by the disclosure, as long as at least one among the plural candidate models is selected according to a configured comparison rule and the final model to be used is built according to the selected candidate model.

Note that compared to the SVM model, the one class SVM model, the random forest model, and/or the logistic classification model, in the decision process of a prediction model related to a time characteristic such as the LSTM model, the LSTM model may further process the time-related characteristic parameter in the physiological characteristic parameters. Therefore, when the prediction model related the time characteristic such as the LSTM model is selected to act as at least one of the at least one candidate model, overall prediction accuracy of the at least one candidate model is improved.

In an embodiment, the prediction model related to the time characteristic such as the LSTM model may further be matched with a deep neural network (DNN) to be designed to produce a LSTM+DNN hybrid model. This hybrid model may also act as one of the at least one candidate model.

In an embodiment, the built prediction model may be further trained. For instance, the operation of obtaining the notable characteristic parameter may be referenced for a training process, and the notable characteristic parameter may be inputted to the prediction model for predicting and training, so that the prediction accuracy of the prediction model is therefore improved. A trained prediction model may accurately evaluate the physiological status of the user.

In an embodiment, after the original electrocardiogram data of a specific user is detected through the manner shown in FIG. 2 or a similar manner, the original electrocardiogram data may be processed by the processor 122, and the corresponding physiological characteristic parameter (or the notable characteristic parameter) may be inputted to the built prediction model. According to the inputted physiological characteristic parameter (or the notable characteristic parameter), the prediction model may generate evaluation data to reflect the physiological status of this user.

Figure 7:
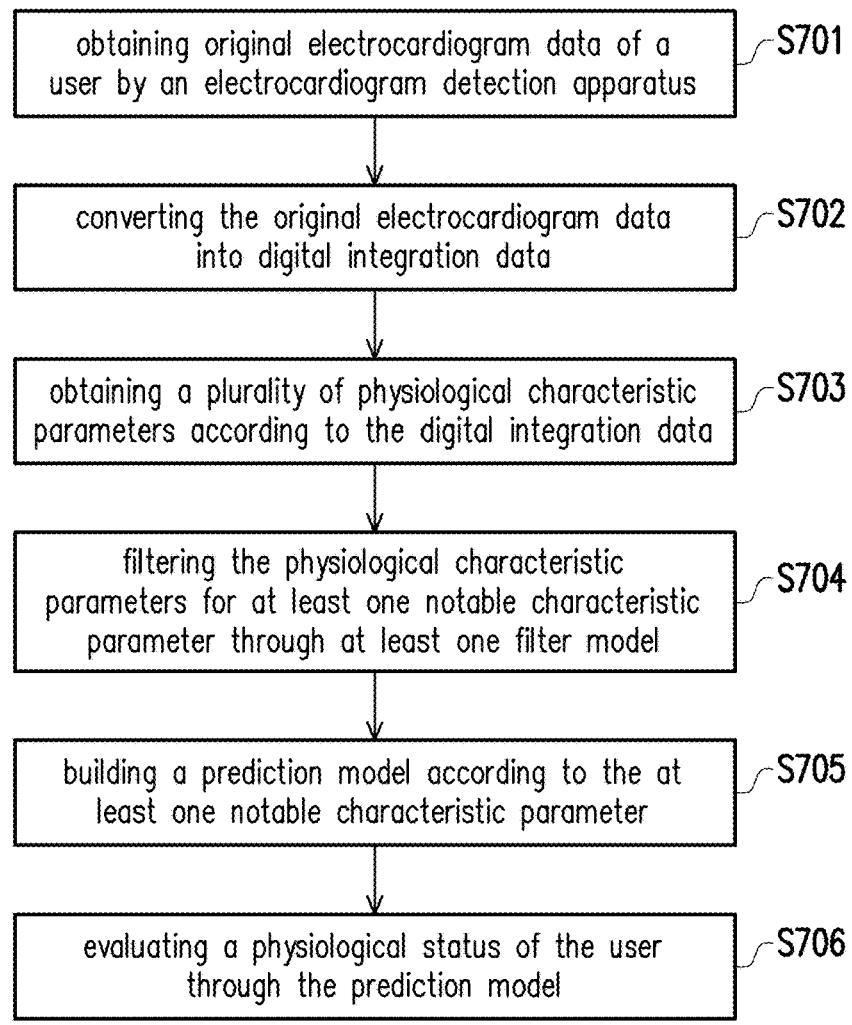
FIG. 7 is a flow chart illustrating a physiological status evaluation method according to an embodiment of the disclosure.

FIG. 7 is a flow chart illustrating a physiological status evaluation method according to an embodiment of the disclosure. With reference to FIG. 7, in step S701, original electrocardiogram data of a user is obtained through an electrocardiogram detection apparatus. In step S702, the original electrocardiogram data is converted into digital integration data. In step S703, a plurality of physiological characteristic parameters are obtained according to the digital integration data. In step S704, the physiological characteristic parameters are filtered for at least one notable characteristic parameter through at least one filter model. Herein, decision importance of the at least one notable characteristic parameter in a decision process of the at least one filter model is greater than a threshold. In step S705, a prediction model is built according to the at least one notable characteristic parameter. In step S706, a physiological status of the user is evaluated through the prediction model.

Figure 8:
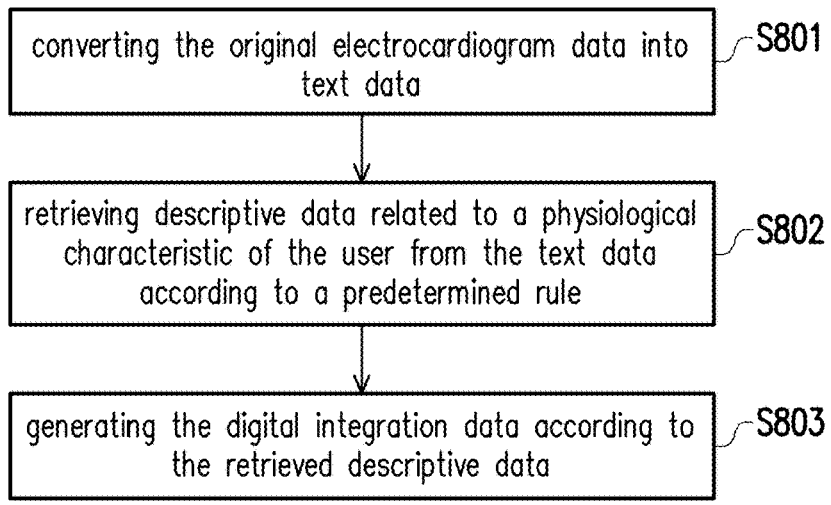
FIG. 8 is a flow chart illustrating the physiological status evaluation method according to an embodiment of the disclosure.

FIG. 8 is a flow chart illustrating the physiological status evaluation method according to an embodiment of the disclosure. With reference to FIG. 8, in step S801, the original electrocardiogram data is converted into text data. In step S802, descriptive data related to a physiological characteristic of the user is retrieved from the text data according to a predetermined rule. In step S803, the digital integration data is generated according to the retrieved descriptive data.

Figure 9:
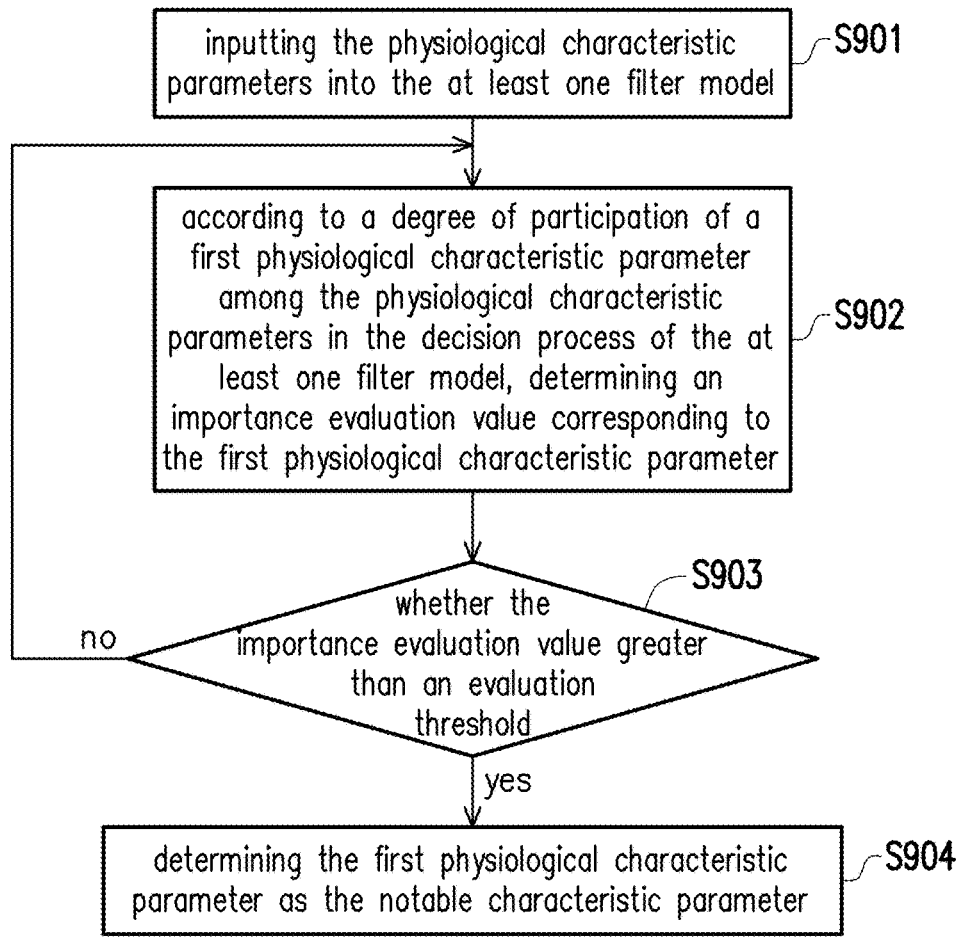
FIG. 9 is a flow chart illustrating the physiological status evaluation method according to an embodiment of the disclosure.

FIG. 9 is a flow chart illustrating the physiological status evaluation method according to an embodiment of the disclosure. With reference to FIG. 9, in step S901, the physiological characteristic parameters are inputted into the at least one filter model. In step S902, according to a degree of participation of a first physiological characteristic parameter among the physiological characteristic parameters in the decision process of the at least one filter model, an importance evaluation value is determined corresponding to the first physiological characteristic parameter. In step S903, it is determined that whether the importance evaluation value is greater than an evaluation threshold. The first physiological characteristic parameter is determined as the notable characteristic parameter if the importance evaluation value is greater than the evaluation threshold. In contrast, if the importance evaluation value is not greater than the evaluation threshold, step S902 may be performed again, importance evaluation values of other physiological characteristic parameters may be continuously obtained, and determination made in step S903 may then be performed.

Figure 10:
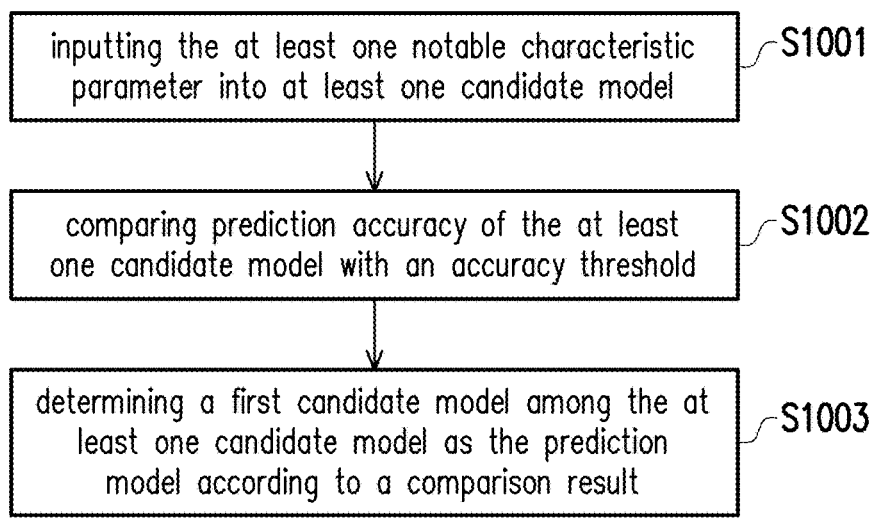
FIG. 10 is a flow chart illustrating the physiological status evaluation method according to an embodiment of the disclosure.

FIG. 10 is a flow chart illustrating the physiological status evaluation method according to an embodiment of the disclosure. With reference to FIG. 10, in step S1001, the at least one notable characteristic parameter is inputted into at least one candidate model. In step S1002, prediction accuracy of the at least one candidate model is compared with an accuracy threshold. In step S1003, according to a comparison result, a first candidate model among the at least one candidate model is determined as a final prediction model to be used.

Nevertheless, each step of FIG. 7 to FIG. 10 is described in detail as above and thus is not repeated hereinafter. Noted that each step in FIG. 7 to FIG. 10 may be implemented as a plurality of program codes or circuits, which is not particularly limited by the disclosure. In addition, the method of FIG. 7 to FIG. 10 may be used in combination with the above-described exemplary embodiments or be used solely, which is not particularly limited by the disclosure.

In view of the foregoing, after the original electrocardiogram data of the user is obtained through the electrocardiogram detection apparatus, the original electrocardiogram data may be converted into the digital integration data. According to the digital integration data, plural physiological characteristic parameters may be obtained. Next, the physiological characteristic parameters are filtered for the at least one notable characteristic parameter through the at least one filter model. In particular, the decision importance of the notable characteristic parameter in a decision process of the filter model is greater than the threshold. Next, one or plural prediction models may be built according to the notable characteristic parameter. In this way, the prediction model may be configured to evaluate the physiological status of the user hereinafter. Accordingly, the evaluation efficiency of the physiological status of the user is therefore improved.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A physiological status evaluation method, comprising:
    obtaining original electrocardiogram data of a user by an electrocardiogram detection apparatus;
    converting, by a processor of a physiological status evaluation apparatus, the original electrocardiogram data into digital integration data;
    obtaining, by the processor, a plurality of physiological characteristic parameters according to the digital integration data;
    filtering, by the processor, the physiological characteristic parameters for at least one notable characteristic parameter through at least one filter model, wherein decision importance of the at least one notable characteristic parameter in a decision process of the at least one filter model is greater than a threshold;
    building, by the processor, a prediction model according to the at least one notable characteristic parameter; and
    evaluating, by the processor, a physiological status of the user through the prediction model.

2. The physiological status evaluation method according to claim 1, wherein the original electrocardiogram data comprises exercise electrocardiogram measurement data.

3. The physiological status evaluation method according to claim 1, wherein the step of converting the original electrocardiogram data into the digital integration data comprises:

converting the original electrocardiogram data into text data;

retrieving descriptive data related to a physiological characteristic of the user from the text data according to a predetermined rule; and generating the digital integration data according to the retrieved descriptive data.

4. The physiological status evaluation method according to claim 3, wherein the step of retrieving the descriptive data related to the physiological characteristic of the user from the text data according to the predetermined rule comprises one of a plurality of following steps:

detecting a keyword in the text data and retrieving first descriptive data corresponding to the keyword;

retrieving second descriptive data in the text data according to a predetermined field format; and detecting a blank data region in the text data and retrieving third descriptive data recorded behind the blank data region.

5. The physiological status evaluation method according to claim 3, wherein the step of converting the original electrocardiogram data into the digital integration data comprises:

obtaining a number of occurrences of predetermined data in the retrieved descriptive data; and verifying whether the digital integration data is valid data according to the number of occurrences.

6. The physiological status evaluation method according to claim 1, wherein the physiological characteristic parameters comprise a time-related characteristic parameter and a logic-related characteristic parameter, the time-related characteristic parameter reflects a physiological characteristic of the user measured at a plurality of time points, and the logic-related characteristic parameter reflects a physiological characteristic of the user matched with a logistic condition.

7. The physiological status evaluation method according to claim 1, wherein the step of filtering the physiological characteristic parameters for the at least one notable characteristic parameter through the at least one filter model comprises:

inputting the physiological characteristic parameters into the at least one filter model;

according to a degree of participation of a first physiological characteristic parameter among the physiological characteristic parameters in the decision process of the at least one filter model, determining an importance evaluation value corresponding to the first physiological characteristic parameter; and determining the first physiological characteristic parameter as one of the at least one notable characteristic parameter if the importance evaluation value is greater than an evaluation threshold.

8. The physiological status evaluation method according to claim 1, wherein the step of building the prediction model according to the at least one notable characteristic parameter comprises:

inputting the at least one notable characteristic parameter into at least one candidate model;

comparing prediction accuracy of the at least one candidate model with an accuracy threshold; and if first prediction accuracy of a first candidate model among the at least one candidate model is greater than the accuracy threshold, determining the first candidate model as the prediction model.

9. The physiological status evaluation method according to claim 8, wherein the at least one candidate model comprises at least one of a long short term memory (LSTM) model, a support vector machine (SVM) model, a one class SVM model, a random forest model, and a logistic classification model.

10. The physiological status evaluation method according to claim 8, wherein the prediction accuracy is presented by at least one of sensitivity, specificity, a positive predictive value (PPV), a negative predictive value (NPV), a positive likelihood ratio (LR+), and a negative likelihood ratio (LR−).

11. A physiological status evaluation apparatus, comprising:

a storage circuit, configured to store original electrocardiogram data of a user obtained by an electrocardiogram detection apparatus;

a processor, coupled to the storage circuit, wherein the processor is configured to convert the original electrocardiogram data into digital integration data, wherein the processor is further configured to obtain a plurality of physiological characteristic parameters according to the digital integration data, wherein the processor is further configured to filter the physiological characteristic parameters for at least one notable characteristic parameter through at least one filter model, wherein decision importance of the at least one notable characteristic parameter in a decision process of the at least one filter model is greater than a threshold, wherein the processor is further configured to build a prediction model according to the at least one notable characteristic parameter, wherein the processor is further configured to evaluate a physiological status of the user through the prediction model.

12. The physiological status evaluation apparatus according to claim 11, wherein the original electrocardiogram data comprises exercise electrocardiogram measurement data.

13. The physiological status evaluation apparatus according to claim 11, wherein an operation of converting the original electrocardiogram data into the digital integration data comprises:

converting the original electrocardiogram data into text data;

retrieving descriptive data related to a physiological characteristic of the user from the text data according to a predetermined rule; and generating the digital integration data according to the retrieved descriptive data.

14. The physiological status evaluation apparatus according to claim 13, wherein an operation of retrieving the descriptive data related to the physiological characteristic of the user from the text data according to the predetermined rule comprises one of a plurality of following operations:

detecting a keyword in the text data and retrieving first descriptive data corresponding to the keyword;

retrieving second descriptive data in the text data according to a predetermined field format; and detecting a blank data region in the text data and retrieving third descriptive data recorded behind the blank data region.

15. The physiological status evaluation apparatus according to claim 13, wherein an operation of converting the original electrocardiogram data into the digital integration data comprises:

obtaining a number of occurrences of predetermined data in the retrieved descriptive data; and verifying whether the digital integration data is valid data according to the number of occurrences.

16. The physiological status evaluation apparatus according to claim 11, wherein the physiological characteristic parameters comprise a time-related characteristic parameter and a logic-related characteristic parameter, the time-related characteristic parameter reflects a physiological characteristic of the user measured at a plurality of time points, and the logic-related characteristic parameter reflects a physiological characteristic of the user matched with a logistic condition.

17. The physiological status evaluation apparatus according to claim 11, wherein an operation of filtering the physiological characteristic parameters for the at least one notable characteristic parameter through the at least one filter model comprises:
 inputting the physiological characteristic parameters into the at least one filter model;
 according to a degree of participation of a first physiological characteristic parameter among the physiological characteristic parameters in the decision process of the at least one filter model, determining an importance evaluation value corresponding to the first physiological characteristic parameter; and
 determining the first physiological characteristic parameter as one of the at least one notable characteristic parameter if the importance evaluation value is greater than an evaluation threshold.

18. The physiological status evaluation apparatus according to claim 11, wherein an operation of building the prediction model according to the at least one notable characteristic parameter comprises:
 inputting the at least one notable characteristic parameter into at least one candidate model;
 comparing prediction accuracy of the at least one candidate model with an accuracy threshold; and
 if first prediction accuracy of a first candidate model among the at least one candidate model is greater than the accuracy threshold, determining the first candidate model as the prediction model.

19. The physiological status evaluation apparatus according to claim 18, wherein the at least one candidate model comprises at least one of a long short term memory (LSTM) model, a support vector machine (SVM) model, a one class SVM model, a random forest model, and a logistic classification model.

20. The physiological status evaluation apparatus according to claim 18, wherein the prediction accuracy is presented by at least one of sensitivity, specificity, a positive predictive value (PPV), a negative predictive value (NPV), a positive likelihood ratio (LR+), and a negative likelihood ratio (LR−).

* * * * *